United States Patent [19]

Vetter

[11] Patent Number: 5,571,882

[45] Date of Patent: Nov. 5, 1996

[54] POLYMERSABLE CARBOHYDRATE ESTERS, POLYMERS THEREFROM AND THEIR USE

[75] Inventor: Dirk Vetter, Freiburg, Germany

[73] Assignee: Ciba-Geiby Corporation, Tarrytown, N.Y.

[21] Appl. No.: 467,248

[22] Filed: Jun. 6, 1995

Related U.S. Application Data

[62] Division of Ser. No. 256,828, Jul. 26, 1994, Pat. No. 5,488,102.

[30] Foreign Application Priority Data

Nov. 30, 1992 [CH] Switzerland ................ 3656/92
Nov. 19, 1993 [WO] WIPO ............. PCT/EP93/03236

[51] Int. Cl.⁶ .............. C12P 19/14; C12P 7/08; C07H 1/00; C07H 3/00
[52] U.S. Cl. ............... 526/238.2; 351/159; 351/160 R; 351/160 H
[58] Field of Search ............... 526/238.2; 351/159, 351/160 R, 160 H

[56] References Cited

U.S. PATENT DOCUMENTS 3,565,887  2/1971  Parmerter ............... 536/103

FOREIGN PATENT DOCUMENTS 890005640  11/1989  Japan .
1134235    5/1968   United Kingdom .

OTHER PUBLICATIONS

"Cyclodextrin–Containing Polymers 1. Prep. of Polymers," Hazada, Aking, et al, *Macromolecules* vol. 9, No. 5, Sep.-Oct. 1976.

"Synthesis of Chemically Modified Cyclodextrins," Croft; Alan, et al. Tetrahedron Report No. 147, Pergamon Press Ltd, pp. 1417–142.

*Primary Examiner*—Nathan M. Nutter
*Attorney, Agent, or Firm*—Edward McC. Roberts; R. Scott Meece

[57] ABSTRACT

Compounds of formulae I and Ia $$R-Y-CO-R_3-CO-O-A \quad \text{(I)},$$

$$R-Y-CO-R_3-CO-O-CH_2-A_1 \quad \text{(Ia)},$$

wherein

R is a radically polymerizable hydrocarbon group, $R_3$ is a direct bond, linear or branched $C_1$–$C_{22}$alkylene, $C_3$–$C_8$cycloalkylene or $C_6$–$C_{14}$arylene, A is the radical, reduced by a hydroxy group in a 2- or 3-position, of a cyclic-oligomeric carbohydrate or of a derivative of such a carbohydrate, $A_1$ is the radical, reduced by a hydroxymethyl group, of a monomeric or linear oligomeric carbohydrate or of a derivative of such a carbohydrate, and Y is —O—, —NH— or —N($C_1$–$C_6$alkyl)-.

Homo- and co-polymers having those monomers have, depending upon their composition, hydrophilic, amphiphilic or hydrophobic properties and are able to form hydrogels. The polymers can be used, for example, as surfactants, thickeners, carriers for biologically active ingredients or in the manufacture of contact lenses.

30 Claims, No Drawings

POLYMERSABLE CARBOHYDRATE ESTERS, POLYMERS THEREFROM AND THEIR USE

This application is a divisional of U.S. application Ser. No. 08/256,828, filed on Jul. 26, 1994, under 35 U.S.C. 120, and now U.S. Pat. No. 5,488,102 which application claims 35 U.S.C. 119 priority to International Application Serial No. PCT/EP93/03236, filed Nov. 19, 1993 and Swiss Patent Application No. 3656/92, filed on Nov. 30, 1992.

The invention relates to polymerisable esters of carbohydrates and dicarboxylic acids having an ester group containing radically polymerisable radicals, to homopolymers and copolymers therefrom, to processes for their preparation and to their use.

The introduction of polymerisable groups into carbohydrates such as, for example, cyclodextrins is desirable owing to their properties, especially their high degree of hydrophilicity, their specific complex-forming behaviour and their bioactivity. Acrylate-containing, methacrylate-containing and cinnamoyl-containing cyclodextrins and polymers therefrom have been described, for example, by A. P. Croft et al. in Tetrahedron, Vol. 39, No. 9, pages 1425 to 1427 (1983). The polymerisable groups are regiospecifically bonded in the 2- or 3-positions. They are obtained by the reaction of suitable activated esters, namely nitrophenylcarboxylic acid esters, with a cyclodextrin. It is generally very difficult completely to remove the resulting nitrophenol, since cyclodextrins form inclusion compounds with those organic compounds. Owing to the fact that nitrophenols are not physiologically acceptable, have a polymerisation-inhibiting action and are also very expensive to purify, polymers from such polymerisable cyclodextrins can be used only to a limited extent.

It is also known to prepare homopolymers or copolymers from acrylate or methacrylate esters of sugars. The acylation of sugars is less regioselective, however, and always results in non-uniform compound mixtures which also comprise compounds having more than one polymerisable acyl group. Polymers from those mixtures therefore always comprise undesired and cross-linked or branched products having a tendency to precipitate out of solutions. In addition, the natural properties of the sugar radicals that are desirable for many applications are lost as a result of multiple substitution. Furthermore, the ester bond of those acrylates and methacrylates is relatively rigid. The areas of application are considerably limited by those disadvantages. In order to obtain regioselectively substituted polymers of an acrylate ester of galactose, it has been proposed to acryloylate the diacetonide of galactose, followed by polymerisation and subsequent unblocking (CA 70:29704p). That complex process is uneconomical, however. WO 91/17255 describes the enzyme-catalysed preparation of polymers from sugars and dicarboxylic acid esters by means of a regioselective diacylation, wherein the sugar radicals are bonded as comonomers in the polymer backbone and, as a consequence, bioactive properties are virtually lost.

It has now been found that cyclosaccharides can be monoacylated regioselectively in the 2- or 3-positions or the primary hydroxy group of monomeric, dimeric or linear oligomeric saccharides can be monoacylated regioselectively, by carrying out the acylation with monovinyl or divinyl esters of dicarboxylic acids. Surprisingly, despite the presence of two ester groups of equal reactivity no dimers or polysubstituted products are obtained. Vinyl ester groups can be transesterified with unsaturated alkanols to form other radically polymerisable monomers or can be amidated with unsaturated amines. Those monomers and the monovinyl esters of sugars are especially suitable for the preparation of linear polymers, the saccharide group being bonded to a flexible spacer. As a consequence of the specific monoacylation and the flexible bonding to a polymer backbone, the properties of the saccharide radicals are largely retained also in the polymers.

The invention relates to compounds of formulae I and Ia

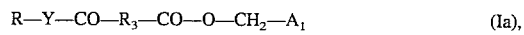

wherein

R is a radically polymerisable hydrocarbon group, $R_3$ is a direct bond, linear or branched $C_1$–$C_{22}$alkylene, $C_3$–$C_8$cycloalkylene or $C_6$–$C_{14}$arylene, A is the radical, reduced by a hydroxy group in a 2- or 3-position, of a cyclic-oligomeric carbohydrate or of a derivative of such a carbohydrate, $A_1$ is the radical, reduced by a hydroxymethyl group, of a monomeric or linear or branched oligomeric carbohydrate or of a derivative of such a carbohydrate, and Y is —O—, —NH— or —N($C_1$–$C_6$alkyl)-.

R preferably contains from 2 to 12, especially from 2 to 10 and more especially from 2 to 8, carbon atoms. The radical R can contain ethene or ethyne groups as radically polymerisable groups. R may be, for example, alkenyl, alkynyl, vinylphenyl or vinylbenzyl. Some examples of alkenyl are vinyl, allyl, 1-propen-2-yl, 1-buten-2- or -3- or -4-yl, 2-buten-3-yl, the isomers of pentenyl, hexenyl, octenyl, decenyl and dodecenyl. Vinyl, allyl and 1-propen-2-yl are preferred. R as alkynyl is preferably an alkynylalkyl radical, for example HCC—$C_mH_{2m}$— or $C_1$–$C_9$alkyl-CC—$C_mH_{2m}$— wherein m is an integer from 1 to 10, preferably from 1 to 6 and especially from 1 to 4, and the total number of carbon atoms is from 3 to 12, preferably from 3 to 8 and especially from 3 to 6. Some examples of alkynyl are propargyl, 1-butyn-3- or -4-yl, 1-pentyn-3- or-4- or-5-yl, 2-pentyn-4- or -5-yl, 1-hexyn-3- or -4- or -5- or -6-yl, 2-hexyn-4- or -5- or -6-yl, and 3-hexyn-5- or -6-yl.

The group Y is preferably —O—, —NH—, -Nmethyl- or -Nethyl- and especially —O— or —NH—.

$R_3$ as alkylene preferably contains from 2 to 20 and especially from 4 to 18 carbon atoms. Some examples are methylene, 1,1-ethylidene, 1,1- or 2,2-propylidene, 1,1- or 2,2-butylidene, 1,1-, 2,2- or 3,3-pentylidene or 1,1-, 2,2- or 3,3-hexylidene, 1,2-ethylene, 1,2- or 1,3-propylene, 1,2-, 1,3-, 2,3- or 1,4-butylene, 1,2-, 1,3-, 1,4-, 1,5-, 2,3-, 2,4- or 2,5-pentylene, 1,2-, 1,3-, 1,4-, 1,5-, 1,6-, 2,3-, 2,4-, 2,5- or 2,6-hexylene, the isomers of heptylene, octylene, nonylene, decylene, undecylene, dodecylene, tridecylene, tetradecylene, pentadecylene, hexadecylene, heptadecylene, octadecylene, nonadecylene and eicosylene.

$R_3$ as cycloalkylene preferably contains from 4 to 6 and especially 5 or 6 carbon atoms. Some examples are cyclopropylene, cyclobutylene, cyclopentylene, cyclohexylene, cycloheptylene and cyclooctylene. $R_3$ as cycloalkylene is preferably 1,2- or 1,3-cyclopentylene and 1,2-, 1,3-and 1,4-cyclohexylene.

$R_3$ as arylene is preferably $C_6$–$C_{14}$arylene. Examples are 1,2-, 1,3- and 1,4-phenylene, 2,3-, 2,7- or 2,8-naphthylene, and biphenylenes of the formula

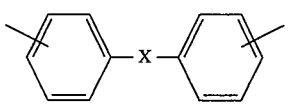

wherein X is a direct bond, —CH$_2$—, CH$_3$CH=, (CH$_3$)$_2$C=, cyclohexylidene, —O—, —S—, —CO—, —CO$_2$—, —SO—, —SO$_2$—, —NH—, —CO—NH—, —N(C$_1$–C$_4$alkyl)- or —CO—N(C$_1$–C$_4$alkyl)-.

In a preferred form, R$_3$ is linear or branched alkylene having from 2 to 20 carbon atoms, especially from 4 to 14 carbon atoms.

Cyclic oligomeric carbohydrates from which the radical A is derived are known. They can contain, for example, from 6 to 8 identical or different monosaccharide units. Examples of monosaccharides are mentioned below. Some preferred examples are α-, β- and γ-cyclodextrin. Derivatives that come into consideration are derivatives substituted in the 6-position by a monosaccharide, oligosaccharide, C$_1$–C$_{12}$alkyl, C$_2$–C$_4$hydroxyalkyl or by C$_1$–C$_{12}$acyl, for example 6-methyl-, 6-hydroxyethyl-, 6-hydroxypropyl-, 6-acetyl- and 6-maltosyl-cyclodextrin.

Within the scope of this invention, monomeric and linear or branched oligomeric carbohydrates are to be understood as being saccharides, for example mono- and oligo-saccharides, such as mono-, di-, tri-, tetra- and penta-saccharides up to deca-saccharides. The oligosaccharides preferably contain from 2 to 8 and especially from 2 to 6 identical or different saccharide units. In a preferred form the mono- and oligo-saccharides are aldoses or ketoses. In an especially preferred form the monosaccharide is an aldopentose, aldohexose, ketopentose or ketohexose.

Examples of an aldopentose are D-ribose, D-arabinose, D-xylose and D-lyxose; examples of an aldohexose are D-allose, D-altrose, D-glucose, D-mannose, D-gulose, D-idose, D-galactose and D-talose; examples of a ketopentose are D-ribulose and D-xylulose; and examples of a ketohexose are D-psicose, D-fructose, D-sorbose and D-tagatose.

Examples of a disaccharide are trehalose, maltose, isomaltose, cellobiose, gentiobiose, saccharose and lactose.

A trisaccharide is, for example, raffinose or panose.

Other oligomers that come into consideration are, for example, oligomeric decomposition products of polysaccharides, for example of starch, dextran, cellulose, curdlan, pullulan and chitin. Somes examples are dextrins, maltotetraose, maltohexaose, and chitoheptaose.

Derivatives of the monomeric and linear or branched oligomeric carbohydrates that may be mentioned are, for example, those substituted in the 1- and/or 2- and/or 3-position(s) by C$_1$–C$_{12}$alkyl, C$_2$–C$_4$hydroxyalkyl and C$_1$–C$_{12}$acyl. Other suitable derivatives are, for example, natural and synthetic nucleosides and also oligonucleotides comprising from 2 to 20, preferably from 2 to 10, such nucleosides which may be identical or different.

In a preferred form, the group R is allyl, propargyl, p-vinylphenyl, p-vinylbenzyl or a radical of the formula R$_1$CH=CR$_2$— wherein R$_1$ is H or C$_1$–C$_6$alkyl and R$_2$ is H, C$_1$–C$_6$alkyl or phenyl.

When R$_1$ is alkyl it preferably contains from 1 to 4 and especially 1 or 2 carbon atoms. The alkyl is preferably linear. Some examples are methyl, ethyl, n-propyl and n-butyl. R$_1$ as alkyl is especially methyl or ethyl.

In a preferred form, R$_1$ is H, methyl or ethyl. R$_1$ is especially H.

When R$_2$ is alkyl it preferably contains from 1 to 4 and especially 1 or 2 carbon atoms. The alkyl is preferably linear.

Some examples are methyl, ethyl, n-propyl, n-butyl, n-pentyl and n-hexyl. R$_2$ is preferably H, methyl, ethyl, propyl or butyl.

In an especially preferred form, R$_1$ is H and R$_2$ is H, methyl, ethyl, n-propyl or n-butyl. R$_1$ and R$_2$ are especially each H.

The invention relates also to a process for the preparation of the compounds of formulae I and Ia, wherein a divinyldicarboxylic acid ester of formula II

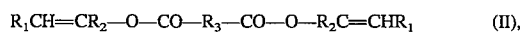

$$R_1CH=CR_2-O-CO-R_3-CO-O-R_2C=CHR_1 \quad (II),$$

or a monovinyl ester of formula IIa

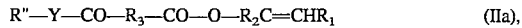

$$R''-Y-CO-R_3-CO-O-R_2C=CHR_1 \quad (IIa),$$

wherein R$_1$ and R$_2$ are as defined below and R$_3$ and Y are as defined above, is (a) transesterified with a cyclic-oligomeric carbohydrate of the formula A—OH, or with a derivative thereof, wherein A is as defined above, or (b) transesterified in the presence of lipolytic enzymes with a monomeric or linear oligomeric carbohydrate of the formula A$_1$—CH$_2$OH, or with a derivative thereof, wherein A$_1$ is as defined above, and (c) if desired the resulting compound of formula I or Ia wherein R is a radically polymerisable vinyl ester group is transesterified or amidated with an alcohol of the formula R'—OH, with an amine R'NH$_2$ or with an amine R'NHC$_1$–C$_4$alkyl, with R' and R'' each independently of the other being a non-vinylic radically polymerisable hydrocarbon group.

The compounds of formula II are known or can be prepared in accordance with known processes, for example in accordance with the procedures described by D. Swern et al., in Organic Synthesis Coll. Vol. IV, Wiley, New York, pp 977–980 (1963) or by E. S. Rothman et al., in J. Org. Chem. 27, pp 3123–3127 (1962). The carbohydrates of the formulae A—OH and A$_1$—CH$_2$OH are likewise known and commercially available.

The transesterification reactions in reaction step (a) are advantageously carried out in a buffer at temperatures of from 0° to 150° C. Inert, polar and water-miscible solvents are advantageously added to the reaction mixture. Suitable solvents are especially alkanols, for example methanol, ethanol, propanol and butanol, or acetone, tetrahydrofuran, dioxane and dimethylformamide. The isolation of the reaction products is effected in a manner known per se, for example by precipitation, filtration and subsequent drying. The products can be purified by elutriation, reprecipitation or by chromatographic methods. The transesterification reactions in reaction step (b) are advantageously carried out in an inert and polar solvent at temperatures of from 0° to 150° C. Suitable solvents are especially diethyl ether, dibutyl ether, tert-butyl methyl ether, tetrahydrofuran, dioxane, acetone, methyl isobutyl ketone, hexane, cyclohexane, methylcyclohexane, benzene, toluene and xylene. The isolation and purification of the products can be carried out as above. Transesterification and amidation reactions in accordance with process step (c) are known to the person skilled in the art. An example of a lipolytic enzyme that may be mentioned is the lipase of *Humicola lanuginosa*. The reactions are advantageously carried out under an inert gas, for example a noble gas or nitrogen.

The compounds of formulae I and Ia are uniform monoacylated monomers having a radically polymerisable group in the ester group which can be polymerised in known manner, for example with the addition of radical initiators, to form linear homopolymers or linear or cross-linked copolymers in which the hydrophilic carbohydrate group is bonded to the polymer backbone by way of a flexible side chain and in which the properties of that group are largely retained.

The invention relates also to polymers that, based on the polymer, comprise i) 0.1 to 100 mol % of at least one structural element of formula III and/or IIIa $$-R_a-$$
$$\quad |$$
$$Y-CO-R_3-CO-O-A, \quad \text{(III)}$$

$$-R_a-$$
$$\quad |$$
$$Y-CO-R_3-CO-O-CH_2-A_1. \quad \text{(IIIa)}$$

wherein $R_a$ is the radical of a radically polymerised group and $R_3$, A, $A_1$ and Y are as defined above, ii) 99.9 to 0 mol % of at least one structural element, different from formulae III and IIIa, of a radically polymerised olefin, and iii) 80 to 0 mol % of at least one structural element of a radically polymerised diolefin, the molar percentages totalling 100%.

The polymers according to the invention can have an average molecular weight (weight average) of from 500 to 2 000 000, preferably from 1000 to 1 000 000 and especially from 1000 to 500 000. The linear polymers according to the invention can have, for example, molecular weights of from 500 to 200 000, preferably from 500 to 100 000 and especially from 500 to 50 000.

$R_a$ preferably contains from 2 to 12, especially from 2 to 10 and more especially from 2 to 8 carbon atoms. The radical $R_a$ may be a trivalent ethanetriyl, phenylene-ethylene, phenylenemethyl-ethylene or ethenetriyl group. The ethanetriyl groups can be unsubstituted or substituted by alkyl, the ethanetriyl groups so substituted preferably containing from 2 to 12, especially from 2 to 10 and more especially from 2 to 8 carbon atoms. Some examples are ethanetriyl, propane-1,2,3-triyl, butane-1,2,4-triyl, pentane-1,2,5-triyl, hexane-1,2,6-triyl, heptane-1,2,7-triyl, octane-1,2,8-triyl, $-CH_2-CH(C_6H_4-)-$ and $-CH_2-CH(C_6H_4CH_2-)-$. The ethenetriyl group can be, for example, a group of the formula $-HC=C(C_mH_{2m}-)-$ or $-(C_1-C_9\text{alkyl})C=C(C_mH_{2m}-)-$ wherein m is an integer from 1 to 10, preferably from 1 to 6 and especially from 1 to 4, and the total number of carbon atoms is from 3 to 12, preferably from 3 to 8 and especially from 3 to 6. An example is $-HC=C(CH_2-)-$.

The arrangements and preferences given above apply to $R_3$, A, $A_1$ and Y.

Component i) can be present, for example, in an amount of from 0.5 to 100 mol %, preferably from 1 to 100 mol %, especially from 5 to 100 mol %, more especially from 10 to 100 mol % and most especially from 20 to 100 mol %. The content of the comonomer units ii) and iii) depends essentially on the desired properties. Component ii) can be present, for example, in an amount of from 99.5 to 0.5 mol %, preferably from 99 to 1 mol %, especially from 95 to 1 mol %, more especially from 90 to 1 mol % and most especially from 80 to 1 mol %. Component iii) can be present, for example, in an amount of from 70 to 0.01 mol %, preferably from 60 to 0.05 mol %, especially from 50 to 0.1 mol %, more especially from 40 to 0.5 mol % and most especially from 30 to 1 mol %.

In a preferred form, the group $R_a$ is a radical of the formula $-CH_2-CH(CH_2-)-$, $-CH_2-CH(C_6H_4-)-$, $-CH_2-CH(C_6H_4CH_2-)-$, $-HC=C(CH_2-)-$ or $-(R_1)CH-C(R_2)=$ wherein $R_1$ is H or $C_1-C_6$alkyl and $R_2$ is H, $C_1-C_6$alkyl or phenyl.

In an especially preferred form, the structural elements of component i) correspond to formula IV or IVa

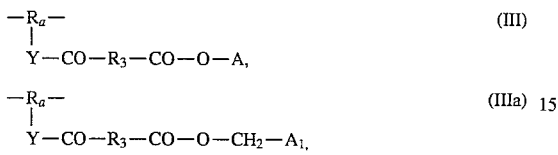

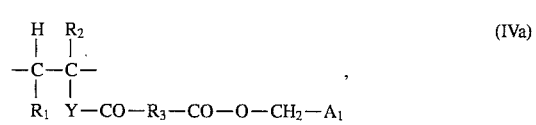

wherein $R_1$ is H or $C_1-C_6$alkyl and $R_2$ is H, $C_1-C_6$alkyl or phenyl, and A, $A_1$, $R_3$ and Y are as defined above, including preferred forms.

When $R_1$ is alkyl it preferably contains from 1 to 4 and especially 1 or 2 carbon atoms. The alkyl is preferably linear. Some examples are methyl, ethyl, n-propyl and n-butyl. $R_1$ as alkyl is especially methyl or ethyl.

In a preferred form, $R_1$ is H, methyl or ethyl. $R_1$ is especially H.

When $R_2$ is alkyl it preferably contains from 1 to 4 and especially 1 or 2 carbon atoms. The alkyl is preferably linear. Some examples are methyl, ethyl, n-propyl, n-butyl, n-pentyl and n-hexyl. $R_2$ is preferably H, methyl, ethyl, propyl or butyl.

In an especially preferred form, $R_1$ is H and $R_2$ is H, methyl, ethyl, n-propyl or n-butyl. $R_1$ and $R_2$ are more especially each H.

Numerous olefin monomers from which the structural elements of component ii) can be derived are known. The olefin monomers are preferably ethylene which is unsubstituted or substituted by halogen, $-OH$, $-CN$, pyrrolidonyl, $C_1-C_{12}$alkyl, phenyl, $C_1-C_4$alkylphenyl, $C_1-C_4$alkoxyphenyl, halophenyl, hydroxyphenyl, $C_1-C_4$alkylhydroxyphenyl, $C_1C_4$alkoxyhydroxyphenyl, chloro- or bromo-hydroxyphenyl, $C_1-C_4$alkoxy, phenoxy, $C_1-C_4$alkylphenoxy, benzyl, benzyloxy, $-COO^{\ominus}M^{\oplus}$, $-COOR_4$, $-COOCH_2CH(OH)CH_2OH$, $-COBR_5-OH$, $-COO-(R_6R_7SiO)_n-SiR_6R_7R_8$, $-COBR_5-O-(R_6R_7SiO)_n-SiR_6R_7R_8$, $-CONH_2$, $-CONH(C_1-C_6\text{alkyl})$, $-CON(C_1-C_6\text{alkyl})_2$ or by $-OCO-R_4$ wherein $M^{\oplus}$ is $H^{\oplus}$, an alkali metal cation or an ammonium cation, $R_4$ is $C_1-C_{18}$alkyl, $C_5-C_7$cycloalkyl, $(C_1-C_{12}\text{alkyl})$-$C_5-C_7$cycloalkyl, phenyl, $(C_1-C_{12}\text{alkyl})$phenyl, benzyl or $(C_1-C_{12}\text{alkyl})$benzyl, $R_5$ is linear or branched $C_2-C_{18}$alkylene, poly($C_2-C_6$oxaalkylene) having from 2 to 6 oxaalkylene units, $C_5-C_8$cycloalkylene, phenylene, benzylene or xylylene, B is $-O-$, $-N(C_1-C_6\text{alkyl})-$ or $-NH-$, $R_6$, $R_7$ and $R_8$ are each independently of the other $C_1-C_6$alkyl or $C_1-C_6$alkoxy and n is a number from 1 to 30.

$R_4$ can be linear or branched $C_1-C_{18}$alkyl, preferably $C_1-C_{12}$alkyl and especially $C_1-C_6$alkyl. $R_4$ as cycloalkyl is especially cyclopentyl or cyclohexyl. When $R_4$ is $(C_1-C_{12}\text{alkyl})$cycloalkyl, the cycloalkyl is especially cyclopentyl or cyclohexyl and the alkyl group can be linear or branched and preferably contains from 1 to 6, especially from 1 to 4, carbon atoms. When $R_4$ is alkylphenyl or alkylbenzyl, the alkyl group can be linear or branched and preferably contains from 1 to 6, especially from 1 to 4, carbon atoms.

$R_5$ as alkylene preferably contains from 2 to 12, especially from 2 to 8 and more especially from 2 to 6, carbon atoms.

Examples are ethylene and the isomers of propylene, butylene, pentylene, hexylene, heptylene, octylene, nonylene, decylene, undecylene, dodecylene, tetradecylene, hexadecylene and octadecylene. Ethylene, 1,2- and 1,3-propylene, 1,2-, 1,3-and 1,4-butylene, 1,2-, 1,3-, 1,4-and 1,5-pentylene and 1,2-, 1,3-, 1,4-, 1,5- and 1,6-hexylene are preferred.

$R_5$ as poly(oxaalkylene) preferably contains from 2 to 4 oxaalkylene units and preferably from 2 to 4, especially 2 or 3, carbon atoms in the alkylene radical.

$R_5$ as cycloalkylene is especially cyclopentylene or cyclohexylene.

$R_6$, $R_7$ and $R_8$ are preferably $C_1$–$C_4$alkyl or $C_1$–$C_4$alkoxy and are especially methyl, ethyl, methoxy or ethoxy. The index n is preferably a number from 1 to 20, especially from 1 to 10.

$M^\oplus$ as an ammonium cation can be, for example, $NH_4^\oplus$ or the cation of a primary amine having from 1 to 12 carbon atoms, of a secondary amine having from 2 to 18 carbon atoms or of a tertiary amine having from 3 to 24 carbon atoms, or is quaternary ammonium having from 4 to 30, preferably from 4 to 20, carbon atoms.

In a preferred form, component ii) comprises structural units of formula IV

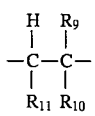
(V)

wherein $R_{11}$ is H, $C_1$–$C_6$alkyl, —$COOR_4$ or —$COO^\ominus M^\oplus$, $R_9$ is H, F, Cl, CN or $C_1$–$C_6$alkyl, $R_{10}$ is H, —F, —Cl, —CN, pyrrolidonyl, $R_{12}O$—, $C_1$–$C_{12}$alkyl, —OH, —$COO^{\ominus M \oplus}$, —$COOR_4$, —$COOCH_2CH(OH)CH_2OH$, —$CONH_2$, —$CONH(C_1$–$C_4$alkyl), —$CON(C_1$–$C_4$alkyl)$_2$, —$COBR_5$—OH, —OCO—$R_4$, —COO—$(R_6R_7SiO)_n$—$SiR_6R_7R_8$, —$COBR_5$—O—$(R_6R_7SiO)_n$—$SiR_6R_7R_8$, phenyl, or phenyl substituted by —OH and/or by one or two methyl, methoxy, Cl or Br, $M^\oplus$ is $H^\oplus$, an alkali metal cation or an ammonium cation, $R_4$ is $C_1$–$C_{18}$alkyl, $C_5$–$C_7$cycloalkyl, $(C_1$–$C_{12}$alkyl)-$C_5$–$C_7$cycloalkyl, phenyl, $(C_1$–$C_{12}$alkyl)phenyl, benzyl or $(C_1$–$C_{12}$alkyl)benzyl, $R_{12}$ is linear or branched $C_2$–$C_{18}$alkylene, poly($C_2$–$C_6$oxaalkylene) having from 2 to 6 oxaalkylene units, $C_5$–$C_8$cycloalkylene, phenylene, benzylene or xylylene, B is —O—, —N($C_1$–$C_4$alkyl)- or —NH—, $R_6$, $R_7$ and $R_8$ are methyl, ethyl, methoxy or ethoxy, and n is 0 or a number from 1 to 20, preferably from 1 to 12.

$R_{11}$ is preferably H. When $R_{11}$ is alkyl it is preferably methyl or ethyl. When $R_{11}$ is —$COOR_4$, $R_4$ is preferably $C_1$–$C_{12}$alkyl, especially $C_1$–$C_6$alkyl.

When $R_9$ is alkyl it is preferably $C_1$–$C_4$alkyl, for example methyl, ethyl, n-propyl and n-butyl. $R_9$ is preferably H, Cl or $C_1$–$C_4$alkyl.

When $R_{10}$ is the group $R_{12}$—O—, $R_{12}$ is preferably $C_1$–$C_{12}$alkyl, especially $C_1$–$C_6$alkyl. When $R_{10}$ is alkyl it preferably contains from 1 to 6, especially from 1 to 4, carbon atoms. When $R_{10}$ is the group —$COOR_4$, $R_4$ is preferably $C_1$–$C_{12}$alkyl, especially $C_1$–$C_6$alkyl, cyclopentyl or cyclohexyl. When $R_{10}$ is the group —OCO—$R_4$, $R_4$ is preferably $C_1$–$C_{12}$alkyl, especially $C_1$–$C_6$alkyl, phenyl or benzyl.

When $R_{10}$ is the group —$COOR_5OH$, the preferences mentioned above for $R_5$ apply.

When $R_{10}$ is a group —$CONH(C_1$–$C_4$alkyl) or —$CON(C_1$–$C_4$alkyl)$_2$, it is preferably —$CONHCH_3$, —$CONHC_2H_5$, $CON(CH_3)_2$ or —$CON(C_2H_5)_2$.

In a preferred form, $R_{11}$ is H, $R_9$ is H, —F, —Cl, methyl or ethyl, and $R_{10}$ is pyrrolidonyl, —F, —Cl, —CN, —OH, $C_1$–$C_4$alkyl, $C_1$–$C_6$alkoxy, —COO—$C_1$–$C_6$alkyl, —COO—$R_5$—OH, —$COOM^\oplus$, —OOC—$C_1$–$C_6$alkyl, —$COOCH_2CH(OH)CH_2OH$, —$CONH_2$, —$CONH(C_1$–$C_4$alkyl), —$CON(C_1$–$C_4$alkyl)$_2$, —COO—$(R_6R_7SiO)_n$—$SiR_6R_7R_8$, —$COBR_5$—O—$(R_6R_7SiO)_n$—$SiR_6R_7R_8$, phenyl, methylphenyl, dimethylphenyl, chlorophenyl, dichlorophenyl, dibromophenyl, methoxyphenyl, dimethoxyphenyl or hydroxyphenyl wherein $M^\oplus$ is trialkylammonium having from 1 to 4 carbon atoms in the alkyl groups and $R_5$ is $C_2$–$C_6$alkylene, and $R_6$, $R_7$ and $R_8$ are methyl, ethyl, methoxy or ethoxy, and n is 0 or a number from 1 to 12.

In a very especially preferred form, in formula V $R_{11}$ is H, $R_9$ is H or methyl, and $R_{10}$ is pyrrolidonyl, —CN, —COOH, —COO—$C_yH_{2y}$—OH wherein y is from 2 to 6, especially 2 or 3, —$CON(CH_3)_2$, —COO—$CH_2CH(OH)CH_2OH$ and —COO—$CH_2CH_2$—O—$[Si(OCH_3)_2$—O$]_n$—$Si(OCH_3)_3$ or —COO—$CH_2CH_2$—O—$[Si(OC_2H_5)_2$—O$]_n$—$Si(OC_2H_5)_3$ wherein n is from 1 to 8 and preferably from 2 to 6.

The copolymers according to the invention can be block polymers, or copolymers having an alternating or statistical distribution of the structural units.

Component iii) can comprise, for example, structural units of butadiene, isoprene and chloroprene. Other suitable structural units can be derived from diacrylates or dimethacrylates of diols or from diacrylamides or dimethacrylamides of diamines. The alcohols and diamines may be those of the formula HY—$C_{xH2x}$—YH wherein x is a number from 2 to 12, preferably from 2 to 6, and Y is —O—, —NH— or —N($C_1$–$C_4$alkyl)-. Suitable diols are also polyoxaalkylenediols of the formula HO—$(C_nH_{2n}O)_y$—H wherein n is a number from 2 to 6, preferably from 2 to 4 and especially 2 or 3, and y is a number from 2 to 20, preferably from 2 to 10, especially from 2 to 6 and more especially from 2 to 4. Some examples are ethylene glycol, 1,2- and 1,3-propylene glycol, 1,2-, 1,3- and 1,4-propylene glycol and the isomers of pentylene glycol, hexylene glycol, heptylene glycol, octylene glycol, nonylene glycol, decylene glycol, undecylene glycol and dodecylene glycol, diethylene glycol, triethylene glycol, tetraethylene glycol, di-1,2-propylene glycol, tri-1,2-propylene glycol, oligomeric polyoxaalkylene glycols having from 4 to 12 identical or different oxaethylene or oxapropylene radicals.

The polymers according to the invention may comprise as a fourth component iiii) up to 10 mol %, preferably from 0.01 to 5 mol %, of radicals of trifunctional ethylenically unsaturated compounds, the molar percentages in the polymer totalling 100 mol %. Examples that may be mentioned are the acrylate and methacrylate triesters of trimethylolpropane or methyltrimethylolpropane.

The preparation of the polymers according to the invention can be carried out in accordance with customary methods by radical polymerisation, including photochemical-radical polymerisation, suitable methods being, for example, block, emulsion, solution or interfacial polymerisation. Isolation and purification can also be carried out in accordance with the methods customary in polymer chemistry. Other details are described in the Examples.

The polymers according to the invention are colourless transparent to white and opaque solids having a very high degree of hydrophilicity. Depending upon the composition, they are water-soluble or are soluble or swellable in water or other dipolar and aprotic or protic solvents, and are able to form gels or hydrogels or non-swellable polymers with strongly hydrophilic surfaces. The polymers may, according to their composition, be hydrophilic, amphiphilic or hydrophobic. The properties of the polymers can be adjusted specifically by the choice and amounts of monomers and of the spacer in the monomers according to the invention. The monomers and polymers are easily obtainable. Some of the polymers are physiologically acceptable and are distinguished by their constant good biological and physicochemical properties. Some of the polymers according to the invention are also biodegradable. These polymers have a wide variety of possible uses in technology.

The polymers according to the invention have film-forming properties. When aqueous or organic solutions are concentrated by evaporation there are formed transparent, solid and possibly water-containing films which are air- and moisture-permeable. On the basis of that property and their water-storing action they are suitable also as moisturisers for the skin or the mucosa in cosmetic preparations and pharmaceutical compositions, as agents for maintaining joint mobility and for wound dressings. Cosmetic preparations are, for example, skin-care and hair-care preparations and deodorants. The polymers according to the invention, and especially gels prepared therefrom, are also suitable for the manufacture of compositions having controlled release of active ingredient over a prolonged period, for example pharmaceutical and pesticidal active ingredients or aromatic substances.

In aqueous solutions the water-soluble polymers according to the invention also have a viscosity-increasing and dispersing action and can be used as surfactants and thickeners. They are suitable, for example, as additives in suspensions, emulsions, dispersions and aqueous solutions, for example in the preparation of foodstuffs or biologically active ingredient concentrates and colouring and pigmenting preparations.

The polymers according to the invention can be used in a manner known per se to prepare films and foils that can be used as membranes or as wound dressings; alternatively, capsules for active ingredients or coated active ingredients can be prepared in a manner known per se, the active ingredient being released into the environment in a delayed and continuous manner.

It is also possible for solid carrier materials, for example metals, semimetals, ceramics, glass, metal and semimetal oxides or nitrides, wood, paper and plastics, to be coated with the polymers according to the invention and for those coated materials to be used, for example, as a base material for sensors.

The polymers according to the invention can be used, for example, also in the manufacture of soft contact lenses from corresponding hydrogels or for the manufacture of hard contact lenses having permanently hydrophilic surfaces or for the modification of the surfaces of contact lenses or for the cleaning of contact lenses.

The invention relates also to the use of the water-soluble polymers according to the invention as thickeners and surfactants.

The invention relates also to the use of the polymers according to the invention as a carrier for active ingredients to provide controlled release of the active ingredient.

The invention relates also to the use of the polymers according to the invention for the manufacture, modification or cleaning of contact lenses.

The following Examples illustrate the invention in more detail.

A) Preparation of Starting Materials

EXAMPLE A1

α,ω-Dicarboxylic Acid Divinyl Esters

The esters are prepared in accordance with the procedure of Swern, D., Jordan, E. F., in Organic Syntheses Coll. Vol. IV, Wiley, New York, 1963, pp 977–980.

Under nitrogen, 2 mol of dicarboxylic acid are suspended in a seven- to eight-fold molar excess of vinyl acetate, and 1 g of $Li(PdCl_2)$ is added. The reaction is started by heating and the addition of a few drops of concentrated sulfuric acid. The mixture is stirred for 20 hours under reflux. Then 1 g of sodium acetate and 10 g of activated carbon are added and the solution is filtered and concentrated. The residue is diluted with 400 ml of diethyl ether, extracted with 5×200 ml of a cold-saturated sodium hydrogen carbonate solution and washed with water. The dried ether phase is filtered and concentrated. For purification, the mixture is separated with dichloromethane over a column of silica gel. The average yields are 50 to 90%.

The following are prepared in that manner: 1,4-divinylbutanedioate, 1,6-divinylhexanedioate, 1,12-divinyldodecanedioate, 1,16-divinylhexadecanedioate, 1,22-divinyldocosanedioate, 4,4'-divinylbiphenyldioate.

α,ω-Dicarboxylic acid diisopropenyl esters are prepared in accordance with the procedure of Rothman, E. S., Serota, S., Perlstein, T., Swern, D., J. Org. Chem. 27 (1962), 3123–3127.

B) Preparation of Monomers

EXAMPLE B1

γ-Cyclodextrinyl-vinyl-hexadecanedioate 2.5 g of γ-cyclodextrin (1.92 mmol) are dissolved in 60 ml of phosphate buffer (0.1 mol/liter, pH 7.0) and 140 ml of ethanol, and 5.0 g of 1,16-divinylhexadecanedioate (17.5 mmol) are added. The mixture is stirred for 68 hours at 50° C. The solution is then concentrated and made up to 300 ml with water. The mixture is extracted twice using 200 ml of diethyl ether each time and the aqueous phase is lyophilised. The crude product is suspended in 25 ml of water, and 150 ml of acetone are added. After filtration and lyophilisation, 0.68 g (23%) of product is obtained.

EXAMPLE B2

β-Cyclodextrinyl-vinyl-dodecanedioate 5 g of β-cyclodextrin (4.4 mmol) are suspended in 120 ml of phosphate buffer (0.1 mol/liter, pH 7.0) and 280 ml of ethanol, and 10.0 g of divinyldodecanedioate (43.4 mmol) are added. The mixture is stirred for 30 hours at 50° C. The solution is then concentrated and made up to a volume of 200 ml with water. The suspension is washed twice using 200 ml of diethyl ether each time and dried on a lyophiliser. The crude mixture is suspended in 50 ml of water, and 270 ml of acetone are added. After lyophilisation, the filtrate yields 2.4 g, of product (40%).

EXAMPLE B3

α-Cyclodextrinyl-vinyl-hexanedioate 50 g of α-cyclodextrin (51 mmol) are dissolved in 3.5 liters of phosphate buffer (0.1 mol/liter, pH 7.0) and 1.5 liters of ethanol, and 50 g of divinylhexanedioate (0.25 mol) are added. The mixture is stirred for 30 hours at 50° C. The solution is then concentrated to 1 liter, filtered and extracted three times using 1 liter of diethyl ether each time. The aqueous phase is lyophilised and the crude product is dissolved in 940 ml of water and reprecipitated with 5.64 liters of acetone. After filtration and concentration to dryness by evaporation, 28.35 g remain which are dissolved in 300 ml of water and stirred with weakly basic anion exchanger (Dowex IRA-93). Lyophilisation of the filtrate yields 17.4 g of product (30%).

$^1$H-NMR (250 MHz, D$_2$O): 1.68 ppm (s, broad, 2(-βCH$_2$-)), 2.43 ppm (s, broad, 2(-αCH$_2$)), 3.33 to 3.95 ppm (cyclodextrin), 4.03 ppm (m, H-3A), 4.92 ppm (s, 5 H-1), 5.11 ppm (d, H-1A), 5.24 ppm (m, H-2A), 7.08 ppm (dr, —HC═CH$_2$).

EXAMPLE B4:

-Cyclodextrinyl-vinyl-hexanedioate 10 g of β-cyclodextrin (7.7 mmol) and 10 g of divinylhexanedioate (50.5 mmol) are suspended in 700 ml of phosphate buffer (0.1 mol/liter, pH 7.0) and 300 ml of ethanol. The solution is heated to 50° C. and stirred or 20 hours and then concentrated to 0.5 liter. After washing three times using 250 ml of diethyl ether each time, the aqueous phase is filtered and lyophilised. The crude mixture is dissolved in 180 ml of water, and 1080 ml of acetone are added. After filtration the solution is concentrated and lyophilised. 6.74 g of product (61%) are obtained.

EXAMPLE B5

α-Cyclodextrinyl-vinyl-butanedioate 1.34 g of α-cyclodextrin (1.37 mmol) are dissolved in 75 ml of phosphate buffer (69 mmol/liter, pH 7.0) and 32 ml of ethanol. After the addition of 2.68 g of divinylbutanedioate (15.75 mmol), the mixture is stirred for 40 hours at 50° C. The mixture is then concentrated to half its volume and adjusted to a volume of 200 ml with water. The solution is washed twice using 200 ml of diethyl ether each time and lyophilised. The crude product is taken up in 32 ml of water, and 192 ml of acetone are added. After filtration and lyophilisation, the substance is dissolved in 68 ml of water and stirred with weakly basic anion exchanger (Amberlite IRA-93). Further filtration and freeze-drying yield 300 mg (20%) of product.

EXAMPLE B6

Maltosylcyclodextrinyl-vinyl-hexanedioate 5 g of maltosylcyclodextrin (3.9 mmol) are dissolved in 350 ml of phosphate buffer (69 mmol/liter, pH 7.0) and 150 ml of ethanol, and 5 g (25 mmol) of divinylhexanedioate are added. After being stirred for 20 hours at 50° C., the mixture is cooled and extracted twice using 250 ml of diethyl ether each time. The aqueous phase is lyophilised and taken up in 91 ml of water. The material that precipitates on the addition of 546 ml of acetone is filtered off and the filtrate is concentrated and dried. 2.2 g of product (39%) are obtained.

EXAMPLES B7 to B13

6-O-glucosyl-vinyl-decanedioate 0.5 g of D-glucose (2.78 mmol), 2.0 g of divinyldecanedioate (7.87 mmol) and 0.5 g of lipase (*Humicola lanuginosa*) are weighed into a container and suspended in 50 ml of acetone. The mixture is stirred for several days at 50° C., then diluted and filtered. Ethyl acetate is added to the filtrate and the precipitate is separated off. The solvents are evaporated off and the residue is taken up in ethyl acetate and hexane is then added. The supernatant is digested. The product is obtained in the form of a pale yellow oil in a yield of 0.924 g (85%). Purification by silica gel column chromatography with dichloromethane/methanol (5:1) yields 48% product.

$^1$H-NMR (250 MHz, deuterated acetone): 1.20 ppm (s, 8 H, γ,γ',δ,δ'-CH$_2$-), 1.48 ppm (m, 4 H, β,β'-CH$_2$-), 2.19 ppm (t, 2 H, α-CH$_2$-), 2.31 ppm (t, 2 H, α-CH$_2$-), 3.19 ppm (m, 2 H, H-4, H-2), 3.57 ppm (t, 1 H, H-3), 3.84 ppm (m, 1 H, H-5), 4.03 ppm (q, 1 H, H-6a), 4.20 ppm (d, 1 H, H-6b), 4.47 ppm (d, 1 H, —CH═CH$_2$ a), 4.72 ppm (d, 1 H, —CH═CH$_2$b), 4.98 ppm (d, 1 H, H-1), 7.17 ppm (dd, 1 H, —CH═CH$_2$).

The products listed in the following Table are prepared in analogous manner.

| Example | Saccharide | Product | Yield |
|---|---|---|---|
| B8 | D-mannose | 6-O-mannosyl-vinyl-decanedioate | 85% |
| B9 | maltose | 6'-O-maltosyl-vinyl-decanedioate | 15% |
| B10 | D-ribose | 5-O-ribosyl-vinyl-decanedioate | 37% |
| B11 | β-methyl-glucoside | 6-O-β-methylglucosidyl-vinyl-octanedioate | 84% |
| B12 | β-octyl-glucoside | 6-O-β-octylglucosidyl-vinyl-octanedioate | 76% |
| B13 | adenosine | 5'-O-adenosyl-vinyl-dodecanedioate | 4% |

C) Preparation of Polymers 3.a) Latex Polymers

In accordance with the Patent Examples of: Nora, I., U.S. Pat. No. 4,735,843, 5th Apr., 1988. In the Patent, oligooleyl ethoxylate ("Volpo 20", Examples 1, 2, 4, 6) and butadiene/ethylene block copolymers (Example 3) are described as emulsifiers for latex polymerisations. Here they are replaced by mono-functionalised cyclodextrins having emulsifying properties (β-cyclodextrinyl vinyldodecanedioate and γ-cyclodextrinyl vinylhexadecanedioate).

EXAMPLE C1

β-Cyclodextrinyl-vinyl-dodecanedioate/isoprene/styrene Latex

Under argon, 120 mg of β-cyclodextrinyl-vinyl-dodecanedioate and 60 mg of potassium peroxodisulfate are weighed into a flask and dissolved in 27 ml of double-distilled water that has been rinsed with argon. 50 μl of dodecylmercaptan, 0.77 ml of styrene and 3.08 ml of isoprene are added thereto. The flask is closed and, with stirring, the reaction is started by heating to 50° C. After 16 hours the latex is obtained in the form of a whitish emulsion.

A transparent, water-resistant and hydrophilic film (contact angle about 45°) is obtained when the latex described according to Example C1 is spread onto a glass surface and dried for 3 days under a current of hot air at 100° C.

EXAMPLES C2 to C13

Under argon, 12 mg of azobis-isobutyronitrile and 200 mg (0.18 mmol) of α-cyclo-dextrinyl-vinyl adipate are weighed into a 5 ml flask and dissolved in 1 ml of argonised solvent. The comonomer (0.36 mmol) is added dropwise, the flask is closed and the mixture is stirred at 60° C. for from 18 to 36 hours. After cooling, the product is precipitated with ethyl acetate and filtered off. A 10% aqueous solution of the residue is treated with five times the volume of acetone and the precipitate is filtered off and dried, and the yield is determined.

The results can be found in the following Table:

| Example | Comonomer | Solvent | Yield (%) | Cyclodextrin/-comonomer | Cyclodextrin content (% by wt.) |
|---|---|---|---|---|---|
| C2 | acrylamide | water/-methanol (1/1) | 55 | 1/33 | 28 |
| C3 | NVP[2] | water/-methanol (1/1) | 80 | 1/10 | 46 |
| C4 | HEMA[3] | water/-methanol (1/1) | 75 | 1/1 | 77 |
| C5 | butyl acrylate | water/-methanol (1/1) | 85 | 2/1 | 85 |
| C6 | butyl acrylate | water/-methanol (1/1) | 80 | 1 | 86 |
| C7 | butyl acrylate | methanol | 65 | 1/1.7 | 72 |
| C8 | styrene | methanol | 72 | 1 | 86 |
| C9 | MAPS[4] | methanol | 71 | 13/1 | 85 |
| C10 | butyl acrylate | dimethylformamide | 61 | 1/1.5 | 74 |
| C11 | MAPS[4] | dimethylformamide | 56 | 14/1 | 85 |
| C12 | styrene | dimethylformamide | 58 | 1 | 86 |
| C13[1] | isoprene | dimethylformamide | 60 | 1/2.2 | 60 |

[1] β-cyclodextrinyl-vinyl-dodecanedioate
[2] N-vinylpyrrolidone
[3] 2-hydroxyethyl methacrylate
[4] 3-methacryloxypropylpentamethyldisiloxane

EXAMPLE C14

Under argon, 12 mg of azobis-isobutyronitrile and 200 mg (0.18 mmol) of α-cyclo-dextrinyl-vinyl adipate are weighed into a 5 ml flask and dissolved in 1 ml of argonised methanol/water (1/1). Hydroxyethyl methacrylate (0.36 mmol) and 10 μl of ethylene glycol bismethacrylate are added and the mixture is stirred at 60° C. for 18 hours. An insoluble, transparent hydrogel is obtained in a yield of 90%.

I claim:

1. A polymer that, based on the polymer, comprises
   I) 0.1 to 100 mol % of a structural element of formula III or IIIa

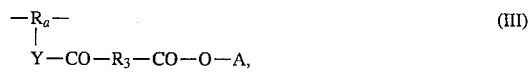

$$-\overset{|}{\underset{Y-CO-R_3-CO-O-A,}{R_a-}}- \quad (III)$$

$$-\overset{|}{\underset{Y-CO-R_3-CO-O-CH_2-A_1,}{R_a-}}- \quad (IIIa)$$

wherein $R_a$ is the radical of a radically polymerised group containing from 2 to 12 carbon atoms, $R_3$ is a direct bond, linear or branched $C_1$–$C_{22}$alkylene, $C_3$–$C_8$cycloalkylene or $C_6$–$C_{14}$arylene, A is a radical, reduced by a hydroxy group in a 2- or 3-position, of a cyclic-oligomeric carbohydrate or of a derivative of such a carbohydrate, $A_1$ is a radical, reduced by a hydroxymethyl group of a monomeric or linear or branched oligomeric carbohydrate or of a derivative of such a carbohydrate, and Y is —O—, —NH—, or —N($C_1$–$C_6$ alkyl)-, ii) 99.9 to 0 mol % of a structural element, different from formulae III and IIIa, of a radically polymerised olefin, and iii) 80 to 0 mol % of a structural element of a radically polymerised diolefin, the molar percentages totalling to 100%.

2. A polymer according to claim 1 wherein the radical $R_a$ is a trivalent ethanetriyl, phenylene-ethylene, phenylenemethyl-ethylene or ethenetriyl group.

3. A polymer according to claim 2 wherein the ethanetriyl group contains up to 12 carbon atoms.

4. A polymer according to claim 2 wherein $R_a$ is ethanetriyl, propane-1,2,3-triyl, butane-1,2,4-triyl, pentane-1,2,5-triyl, hexane-1,2,6-triyl, heptane-1,2,7-triyl, octane-1,2,8-triyl, —CH$_2$—CH(C$_6$H$_4$—)— or —CH$_2$—CH(C$_6$H$_4$CH$_2$—)—.

5. A polymer according to claim 2 wherein the ethenetriyl group is a group of the formula —HC=C(C$_m$H$_{2m}$—)— or —(C$_1$–C$_9$alkyl)C=C(C$_m$H$_{2m}$—)— wherein m is an integer from 1 to 10 and the total number of carbon atoms is from 3 to 12.

6. A polymer according to claim 5 wherein $R_a$ is —HC=C(CH$_2$—)—.

7. A polymer according to claim wherein $R_a$ is a radical of the formula —CH$_2$—CH(CH$_2$—)—, —CH$_2$—CH(C$_6$H$_4$—)—, —CH$_2$—CH(C$_6$H$_4$CH$_2$—)—, —HC=C(CH$_2$—)— or —(R$_1$)CH—C(R$_2$)= wherein R$_1$ is H or C$_1$–C$_6$alkyl and R$_2$ is H, C$_1$–C$_6$alkyl or phenyl.

8. A polymer according to claim 1 wherein component i) is present in an amount of from 0.5 to 100 mol %.

9. A polymer according to claim 1 wherein component ii) is present in an amount of from 99.5 to 0.5 mol %.

10. A polymer according to claim 1 wherein component iii) is present in an amount of from 70 to 0.01 mol %.

11. A polymer according to claim 1 wherein the structural elements of component i) correspond to formula IV and/or IVa

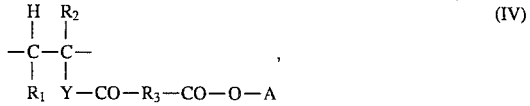

$$\begin{array}{c} H \quad R_2 \\ | \quad | \\ -C-C- \\ | \quad | \\ R_1 \quad Y-CO-R_3-CO-O-A \end{array} \quad (IV)$$

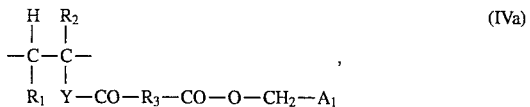

$$\begin{array}{c} H \quad R_2 \\ | \quad | \\ -C-C- \\ | \quad | \\ R_1 \quad Y-CO-R_3-CO-O-CH_2-A_1 \end{array} \quad (IVa)$$

wherein R$_1$ is H or C$_1$–C$_6$alkyl and R$_2$ is H, C$_1$–C$_6$alkyl or phenyl, and A, A$_1$, R$_3$ and Y are as defined in claim 1.

12. A polymer according to claim 11 wherein R$_1$ is H and R$_2$ is H, methyl, ethyl, n-propyl or n-butyl.

13. A polymer according to claim 11 wherein R$_1$ and R$_2$ are each H.

14. A polymer according to claim 1 wherein the olefin monomers from which the structural elements of component ii) are derived are ethylene which is unsubstituted or substituted by halogen, —OH, —CN, pyrrolidonyl, $C_1$–$C_{12}$alkyl, phenyl, $C_1$–$C_4$alkylphenyl, $C_1$–$C_4$alkoxyphenyl, halophenyl, hydroxyphenyl, $C_1$–$C_4$alkylhydroxyphenyl, $C_1$–$C_4$ alkoxyhydroxyphenyl, chloro- or bromo-hydroxyphenyl, $C_1$–$C_4$alkoxy, phenoxy, $C_1$–$C_4$alkylphenoxy, benzyl, benzyloxy, —COO$^\ominus$M$^\oplus$, —COOR$_4$, —COOCH$_2$CH(OH)CH$_2$OH, —COBR$_5$—OH, —COO—(R$_6$R$_7$SiO)$_n$—SiR$_6$R$_7$R$_8$, —COBR$_5$—O—(R$_6$R$_7$SiO)$_n$—SiR$_6$R$_7$R$_8$, —CONH$_2$, —CONH(C$_1$–C$_6$alkyl), —CON(C$_1$–C$_6$alkyl)$_2$ or by —OCO—R$_4$ wherein M$^\oplus$ is H$^\oplus$, an alkali metal cation or an ammonium cation, $R_4$ is $C_1$–$C_{18}$alkyl, $C_5$–$C_7$cycloalkyl, ($C_1$–$C_{12}$alkyl)-C$_5$–$C_7$cycloalkyl, phenyl, ($C_1$–$C_{12}$alkyl)phenyl, benzyl or ($C_1$–$C_{12}$alkyl)benzyl, $R_5$ is linear or branched $C_2$–$C_{18}$alkylene, poly($C_2$–$C_6$oxaalkylene) having from 2 to 6 oxaalkylene units, $C_5$–$C_8$cycloalkylene, phenylene, benzylene or xylylene, B is —O—, —N(C$_1$–C$_6$alkyl)- or —NH—, $R_6$, $R_7$ and $R_8$ are each independently of the other $C_1$–$C_6$alkyl or $C_1$–$C_6$alkoxy and n is a number from 1 to 30.

15. A polymer according to claim 14 wherein $R_4$ as alkyl is $C_1$–$C_6$alkyl.

16. A polymer according to claim 14 wherein $R_5$ as alkylene contains from 2 to 6 carbon atoms.

17. A polymer according to claim 14 wherein $R_6$, $R_7$ and $R_8$ are methyl, ethyl, methoxy or ethoxy.

18. A polymer according to claim 14 wherein M$^\oplus$ as an ammonium cation is NH$_4^\oplus$ or the cation of a primary amine having from 1 to 12 carbon atoms, of a secondary amine having from 2 to 18 carbon atoms, or of a tertiary amine having from 3 to 24 carbon atoms, or is quaternary ammonium having from 4 to 30, preferably from 4 to 20, carbon atoms.

19. A polymer according to claim 14 wherein component ii) comprises structural units of formula V

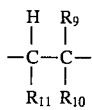

(V)

wherein $R_{11}$ is H, $C_1$–$C_6$alkyl, —COOR$_{20}$ or —COO$^\ominus$M$^\oplus$, $R_9$ is H, F, Cl, CN or $C_1$–$C_6$alkyl, $R_{10}$ is H, F, Cl, CN, pyrrolidonyl, R$_{12}$O—, $C_1$–$C_{12}$alkyl, —OH, —COO$^\ominus$M$^\oplus$, —COOR$_4$, —COOCH$_2$CH(OH)CH$_2$OH, —CONH$_2$, —CONH(C$_1$–C$_4$alkyl), —CON(C$_1$–C$_4$alkyl)$_2$, —COBR$_5$—OH, —OCO—R$_4$, —COO—(R$_6$R$_7$SiO)$_n$—SiR$_6$R$_7$R$_8$, —COBR$_5$—O—(R$_6$R$_7$SiO)$_n$—SiR$_6$R$_7$R$_8$, phenyl, or phenyl substituted by —OH and/or by one or two methyl, methoxy, Cl or Br, M$^\oplus$ is H$^\oplus$, an alkali metal cation or an ammonium cation, $R_4$ is $C_1$–$C_{18}$alkyl, $C_5$–$C_7$cycloalkyl, ($C_1$–$C_{12}$alkyl)-$C_5$–$C_7$ cycloalkyl, phenyl, ($C_1$–$C_{12}$alkyl)phenyl, benzyl or ($C_1$–$C_{12}$alkyl)benzyl, $R_{12}$ is linear or branched $C_2$–$C_{18}$alkylene, poly($C_2$–$C_6$oxaalkylene) having from 2 to 6 oxaalkylene units, $C_5$–$C_8$cycloalkylene, phenylene, benzylene or xylylene, B is —O—, —N(C$_1$–C$_4$alkyl)- or —NH—, $R_6$, $R_7$ and $R_8$ are methyl, ethyl, methoxy or ethoxy, and n is 0 or a number from 1 to 20, preferably from 1 to 12.

20. A polymer according to claim 19 wherein $R_{11}$ is H.

21. A polymer according to claim 19 wherein $R_9$ is H, Cl or $C_1$–$C_4$alkyl.

22. A polymer according to claim 19 wherein $R_{11}$ is H, $R_9$ is H, F, Cl, methyl or ethyl, and $R_{10}$ is pyrrolidonyl, —F, —Cl, —CN, —OH, $C_1$–$C_4$alkyl, $C_1$–$C_6$alkoxy, —COO—$C_1$–$C_6$alkyl, —COO—R$_5$—OH, —COOM$^\oplus$, —OOC—$C_1$–$C_6$alkyl, —COOCH$_2$CH(OH)CH$_2$OH, —CONH$_2$, —CONH(C$_1$–C$_4$alkyl), —CON(C$_1$–C$_4$alkyl)$_2$, —COO—(R$_6$R$_7$SiO)$_n$—SiR$_6$R$_7$R$_8$, —COBR$_5$—O—(R$_6$R$_7$SiO)$_n$—SiR$_6$R$_7$R$_8$, phenyl, methylphenyl, dimethylphenyl, chlorophenyl, dichlorophenyl, dibromophenyl, methoxyphenyl, dimethoxyphenyl or hydroxyphenyl wherein M$^\oplus$ is trialkylammonium having from 1 to 4 carbon atoms in the alkyl groups and $R_5$ is $C_2$–$C_6$alkylene, and $R_6$, $R_7$ and $R_8$ are methyl, ethyl, methoxy or ethoxy, and n is 0 or a number from 1 to 12.

23. A polymer according to claim 19 wherein in formula V $R_{11}$ is H, $R_9$ is H or methyl, and $R_{10}$ is pyrrolidonyl, —CN, —COOH, —COO—$C_yH_{2y}$—OH wherein y is from 2 to 6, —CON(CH$_3$)$_2$, —COO—CH$_2$CH(OH)CH$_2$OH and —COO—CH$_2$CH$_2$O—[Si(OCH$_3$)$_2$—O]$_n$—Si(OCH$_3$)$_3$ or —COO—CH$_2$CH$_2$—O—[Si(OC$_2$H$_5$)$_2$—O]$_n$—Si(OC$_2$H$_5$)$_3$ wherein n is from 1 to 8 and preferably from 2 to 6.

24. A polymer according to claim 1 wherein component iii) comprises structural units of butadiene, isoprene and chloroprene.

25. A polymer according to claim 1 wherein component iii) comprises structural units derived from diacrylates or dimethacrylates of diols or from diacrylamides or dimethacrylamides of diamines.

26. A polymer according to claim 25 wherein the diols and diamines are those of the formula HY—$C_xH_{2x}$—YH wherein x is a number from 2 to 12, and Y is —O—, —NH— or —N(C$_1$–C$_4$alkyl)-, or polyoxaalkylenediols of the formula HO—(C$_m$H$_{2m}$O)$_y$—H wherein m is a number from 2 to 6 and y is a number from 2 to 20.

27. A contact lens comprising a polymer according to claim 1.

28. A contact lens consisting of a polymer according to claim 1.

29. A contact lens having an outer layer of a polymer according to claim 1.

30. A polymer according to claim 1 comprising as fourth component iiii) up to 10 mol % of radicals of a compound having three ethylenically unsaturated groups, the molar percentages totalling 100%.

\* \* \* \* \*